United States Patent
Ham et al.

(10) Patent No.: US 11,554,149 B2
(45) Date of Patent: Jan. 17, 2023

(54) METHOD OF CONTINUOUSLY PRODUCING CANNABIDIOL FROM CANNABIS PLANT AND USE THEREOF

(71) Applicant: KOREA INSTITUTE OF SCIENCE AND TECHNOLOGY, Seoul (KR)

(72) Inventors: Jungyeob Ham, Gangneung-si (KR); Taejung Kim, Gangneung-si (KR); Bong Chul Chung, Seoul (KR); Seok Lee, Seoul (KR); Bong Geun Song, Gangneung-si (KR); Sungdo Ha, Gangneung-si (KR); Young Tae Park, Gangneung-si (KR); Pilju Choi, Gangneung-si (KR); Hoon Ryu, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 85 days.

(21) Appl. No.: 17/035,690

(22) Filed: Sep. 29, 2020

(65) Prior Publication Data

US 2021/0100864 A1    Apr. 8, 2021

(30) Foreign Application Priority Data

Oct. 4, 2019    (KR) .................. 10-2019-0123362

(51) Int. Cl.
| | |
|---|---|
| A61K 36/185 | (2006.01) |
| A23L 33/105 | (2016.01) |
| A61K 8/9789 | (2017.01) |
| A61K 8/34 | (2006.01) |
| A61K 31/05 | (2006.01) |
| B01J 19/12 | (2006.01) |

(52) U.S. Cl.
CPC .......... *A61K 36/185* (2013.01); *A23L 33/105* (2016.08); *A61K 8/347* (2013.01); *A61K 8/9789* (2017.08); *A61K 31/05* (2013.01); *B01J 19/126* (2013.01); *A61K 2236/331* (2013.01); *A61K 2236/333* (2013.01); *B01J 2219/00065* (2013.01); *B01J 2219/00141* (2013.01)

(58) Field of Classification Search
None
See application file for complete search history.

(56) References Cited

U.S. PATENT DOCUMENTS

| | | | |
|---|---|---|---|
| 9,981,203 B2 | 5/2018 | Shuja | |
| 10,143,706 B2 * | 12/2018 | Kotra | ............... A61K 31/775 |
| 2018/0000857 A1 * | 1/2018 | Kotra | ................. A61P 25/00 |
| 2018/0296616 A1 | 10/2018 | Rivas | |
| 2018/0362429 A1 | 12/2018 | Zhang et al. | |
| 2020/0080021 A1 | 3/2020 | Thomas | |

FOREIGN PATENT DOCUMENTS

| | | |
|---|---|---|
| CN | 106278828 A | 1/2017 |
| CN | 110156567 A | 8/2019 |
| CN | 110156568 A | 8/2019 |
| KR | 1020190088994 A | 7/2019 |
| KR | 1020190098648 A | 8/2019 |
| WO | 2018000094 A1 | 1/2018 |
| WO | 2019/119153 A1 | 6/2019 |

OTHER PUBLICATIONS

Bagley et al. (2005) J. Org. Chem. 70: 7003-7006. (Year: 2005).*
Chang et al. (2017) Molecules 22: 1894 (15 pages) (Year: 2017).*
Estel et al. (2017) Chemical Engineering and Proc. 113: 56-64. (Year: 2017).*
Hoskin et al. (2022) Future Foods 5: 100137. (Year: 2022).*
Marszalek et al. (2015) Food Bioprocess. Technol. 8: 1864-1876. (Year: 2015).*
Radoiu et al. (2020) Technologies 8, 45 (16 pages). (Year: 2020).*
Subratti et al. (2019) Sustainable Chemistry and Pharmacy 12: 100144 (6 pages). (Year: 2019).*
Lewis-Bakker et al., "Exactions of Medical Cannabis Cultivars and the Role of Decarboxylation in Optimal Receptor Responses," Cannabis and Cannabinoid Research, Sep. 2019, pp. 183-194, vol. 4, No. 3.
The extended European Search Report for EP Application No. 20199737.6 dated Feb. 25, 2021, citing the above reference(s).
Boldor et al., "Microwave Assisted Extraction of Biodiesel Feedstock from the Seeds of Invasive Chinese Tallow Tree", Environ. Sci. Technol., 2010, pp. 4019-4025, vol. 44, No. 10.
Korean Office Action for KR Application No. 10-2019-0123362 dated Nov. 26, 2020, citing the above reference(s). In conformance with MPEP 609—Concise explanation of the relevance includes issue date of KR OA and references cited therein.

* cited by examiner

*Primary Examiner* — Russell G Fiebig
(74) *Attorney, Agent, or Firm* — Cantor Colburn LLP

(57) ABSTRACT

Provided are: a method of preparing a cannabis processed product having an increased CBD content in an efficient and economic manner, through a decarboxylation reaction by continuous microwave irradiation of a cannabis extract; and use of a processed product having an increased CBD content prepared by the method, a fraction thereof, and a single ingredient of CBD, in foods, drugs, and cosmetics.

11 Claims, 11 Drawing Sheets

METHOD OF CONTINUOUSLY PRODUCING CANNABIDIOL FROM CANNABIS PLANT AND USE THEREOF

CROSS-REFERENCE TO RELATED APPLICATION

This application is based on and claims priority under 35 U.S.C. § 119 to Korean Patent Application No. 10-2019-0123362, filed on Oct. 4, 2019, in the Korean Intellectual Property Office, the disclosure of which is incorporated by reference herein in its entirety.

BACKGROUND

1. Field

The present disclosure relates to a continuous preparation method for increasing the cannabidiol (CBD) content from *Cannabis sativa* L. and an extract thereof using microwaves, and use thereof.

2. Description of Related Art

Cannabis (*Cannabis sativa* L.) is an annual plant belonging to the genus *Cannabis* in the family Cannabaceae, which has been widely cultivated in temperate and tropical areas, mainly in Central Asia, for 12,000 years, and includes wild-type cannabis, and collectively refers to *cannabis chemovars*, which contain different kinds of cannabinoid compounds known as medical/pharmaceutical ingredients, and variants thereof, *Cannabis sativa* subspecies *sativa* including variants var. *indica* and var. *kafiristanica, Cannabis sativa* subspecies *indica, Cannabis sativa* subspecies *ruderalis*, and plants which are the result of genetic crosses, self-crosses, or hybrids thereof.

According to Korean and Chinese traditional medical records, mazain (麻子仁) or hwamain (火麻仁), which is a peeled seed of cannabis, has been used for constipation, diabetes, pain diseases, menstrual disorders, skin diseases, dysentery, etc., and cannabis weed which is a cannabis leaf has been used for anthelmintic, hair protection, asthma, analgesic, anesthetic, diuretic purposes, etc. Further, cannabis root has been used to treat difficult births and to relieve blood stasis, cannabis skin has been used for bruises, irritating rashes and distending pain, cannabis flower has been used for paralysis, itching, etc., and cannabis flower neck has been used for difficult births, constipation, gout, insanity, insomnia, etc. There are records that each part of cannabis were appropriately used according to the condition.

Cannabis includes about 400 compounds, and most of them are cannabinoids, terpenes, and phenolic compounds. There are about 90 kinds of cannabinoids, which are medically/pharmacologically important natural ingredients, and there are many ingredients found only in cannabis.

Among the cannabinoids of cannabis, a psychotropic ingredient is $\Delta^9$-tetrahydrocannabinol ($\Delta^9$-THC), and cannabidiol (CBD), which is a non-psychotropic ingredient, are known to exhibit physiologically active effects through various receptors in the human body, including adrenergic receptors and cannabinoid receptors.

In particular, while scientists were studying the mechanism of psychotropic action of cannabis, in 1988, they discovered a receptor in the brain to which cannabinoid selectively binds, indicating that molecules similar to cannabinoids are also produced in the body. These cannabinoid molecules are fatty acid-type neurotransmitters locally produced in the brain, and also called anandamide. Currently known cannabis receptors are divided into two types. CB1 receptors are distributed throughout the brain, including in the cerebral cortex, hippocampus, cerebellum, basal ganglia, etc. CB2 receptors are mainly distributed in macrophages or peripheral tissues such as bone marrow, lungs, pancreas, smooth muscle, etc., and are closely related to the immune system.

THC is a main active ingredient of cannabis used for medicinal purposes. THC is an agonist with a strong affinity for CB1 receptors, and is known to exhibit a main mechanism of psychotropic action. Many experimental results have revealed that CBD has beneficial effects such as anti-inflammatory action, antiepileptic action, antiemetic action, anti-cancer action, etc. Further, CBD reduces the negative effects of THC, and inhibits reuptake and breakdown of anandamide, which is an endogenous cannabinoid, through antagonistic action on CB1 and CB2 receptor agonists such as THC, and is also known as a serotonin receptor agonist. It was also revealed that cannabichromene, which is an ingredient of cannabis, has anti-inflammatory, sedative, antifungal actions, etc., and cannabinol (CBN) helps boost immune function by binding to CB2 receptors rather than CB1 receptors, and much research has been very actively conducted on pharmacological mechanisms of ingredients included in cannabis.

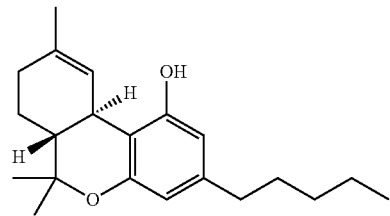 [SMILES: CCCCCc1cc(O)c2c(c1)OC(C)(C)[C@@H]1CCC(C)=C[C@@H]21]

$\Delta^9$-Tetrahydrocannabinol, $\Delta^9$-THC

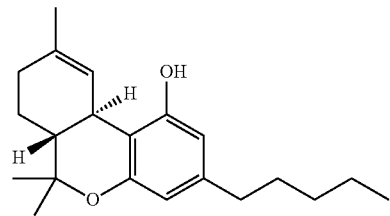 [SMILES: CCCCCc1cc(O)c2c(c1)OC(C)(C)[C@@H]1CCC(C)=C[C@@H]21]

$\Delta^8$-Tetrahydrocannabinol, $\Delta^8$-THC

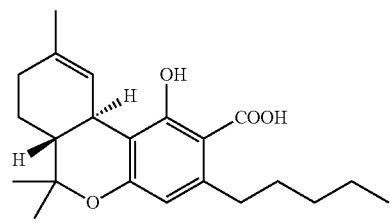 [SMILES: CCCCCc1cc2c(c(O)c1C(=O)O)[C@@H]1C=C(C)CC[C@H]1C(C)(C)O2]

$\Delta^9$-Tetrahydrocannabinolic acid, $\Delta^9$-THCA

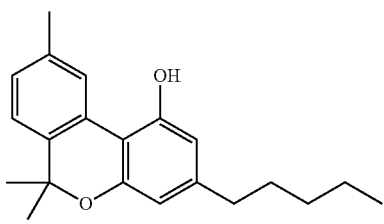 [SMILES: CCCCCc1cc(O)c2c(c1)OC(C)(C)c1ccc(C)cc1-2]

Cannabinol, CBN

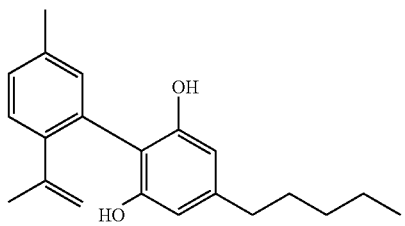 [SMILES: C=C(C)c1ccc(C)cc1-c1c(O)cc(CCCCC)cc1O]

Cannabinodiol, CBND

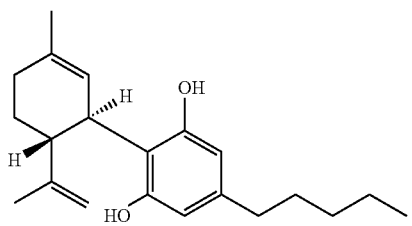 [SMILES: C=C(C)[C@@H]1CCC(C)=C[C@H]1c1c(O)cc(CCCCC)cc1O]

Cannabidiol, CBD

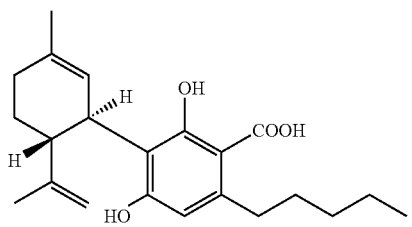 [SMILES: C=C(C)[C@@H]1CCC(C)=C[C@H]1c1c(O)cc(CCCCC)c(C(=O)O)c1O]

Cannabidiolic acid, CBDA

Dronabinol (brand name: Marinol) and nabilone (brand name: Cesamet), which are oral forms of THC approved by the US Food and Drug Administration (FDA), are being sold as relievers for chemotherapy-induced side-effects and as appetite stimulants for AIDS patients, and extensive studies have been actively conducted, such as clinical trials for Epidiolex which is a liquid drug including CBD as a main ingredient for children with epilepsy, Resunab which is a CB2 receptor-binding synthetic cannabinoid formulation for the treatment of systemic lupus erythematosus, and Cannador (THC:CBD=2:1) which is not a single THC or CBD drug but in the form of a cannabis extract for the treatment of multiple sclerosis and severe chronic pain disorders, etc.

Accordingly, the present inventors have developed technologies to increase extraction yields of the main pharmaceutical ingredients of cannabis and to increase the content of CBD using microwave processing technology that has been accumulated so far, and as a result, have found that CBD is easily converted from CBDA through a microwave-assisted decarboxylation reaction while continuously applying a reaction mixture, thereby completing the present disclosure.

SUMMARY

An aspect provides a method of isolating cannabinoid from a *Cannabis* sp. plant or an extract thereof.

Another aspect provides an antiepileptic, neuroprotective, vasorelaxant, anti-cancer, anti-inflammatory, anti-diabetic, anti-bacterial, analgesic, anti-osteoporosis, immune-enhancing, or antiemetic pharmaceutical composition, the pharmaceutical composition including, as an active ingredient, the cannabinoid isolated by the above method.

Still another aspect provides a health functional food composition including, as an active ingredient, the cannabinoid isolated by the above method.

Still another aspect provides a cosmetic composition including, as an active ingredient, the cannabinoid isolated by the above method.

Additional aspects will be set forth in part in the description which follows and, in part, will be apparent from the description, or may be learned by practice of the presented embodiments of the disclosure.

An aspect provides a method of continuously producing cannabinoid, the method including irradiating microwaves to a reaction mixture including a sample including CBDA and a solvent in a reaction vessel, wherein the microwave irradiation is carried out while passing the reaction mixture from an inlet of the reaction vessel and out through an outlet of the reaction vessel. The method may further include isolating cannabinoid from the microwave-irradiated reaction mixture. The sample including CBDA may be a plant including CBDA, for example, a *Cannabis* sp. plant or an extract thereof. The sample may include CBDA of 1%, 3%, 5%, 10%, 15%, or 20% or more with respect to the weight of the sample.

An aspect provides a method of continuously producing cannabinoid, the method including irradiating microwaves to a reaction mixture including a *Cannabis* sp. plant or an extract thereof and a solvent in a reaction vessel, wherein the microwave irradiation is carried out while passing the reaction mixture from an inlet of the reaction vessel and out through an outlet of the reaction vessel. The method may further include isolating cannabinoid from the microwave-irradiated reaction mixture.

In the method, the reaction vessel may have a tubular shape and its length in the flow direction of the reaction mixture may be longer than its height. The height may be a length in the direction perpendicular to the flow direction of the reaction mixture. The length in the flow direction may be 0.5 times, 1 times, 2 times, 3 times, 4 times, 5 times, 10 times, 15 times, 50 times, 100 times, 1000 times, 1500 times, 2000 times, 5000 times, 10,000 times, 0.5 times to 10,000 times, 1.0 times to 10,000 times, 5 times to 10,000 times, 10 times to 10,000 times, 100 times to 10,000 times, or 1000 times to 10,000 times the height. The height may be 0.01 cm to 3.0 cm. The height may be the inside diameter of the tube. Further, the length in the flow direction may be 1.0 cm to 30,000 cm. The reaction vessel may be at least partially or entirely made of a microwave-transparent or semi-transparent material. The microwave-transparent material refers to a material that passes a substantial portion of microwave energy irradiated from a microwave generator and allows it to reach the inside of the reaction vessel. The microwave-transparent material may be, for example, thermoplastics, glass, or a combination thereof. The microwave-transparent material may be Teflon such as glass-filled Teflon, polytetrafluoroethylene (PTFE), and perfluoroalkoxy alkanes (PFA), poly(methyl methacrylate) (PMMA), polyetherimide (PEI), aluminum oxide, glass, or a combination thereof.

The reaction vessel may include an inlet and an outlet, and a channel through which a fluid may flow may be connected to the outlet, and a pump capable of applying a pressure to the fluid and a pressure regulator, for example, back pressure regulator may be connected to the channel, respectively. The pressure regulator may be a back pressure regulator. The reaction vessel may be connected to a temperature controller for controlling the temperature inside the reaction vessel. The temperature controller may be a chamber including the reaction vessel and may include a liquid medium. In irradiating microwaves to the reaction mixture included in the reaction vessel, when the microwave is required to pass through the chamber including the reaction vessel, the chamber may include the microwave-transparent material. The chamber may have any shape as long as it includes the reaction vessel, for example, a long pipe or tube.

The liquid medium is a liquid medium capable of transferring heat to the reaction vessel. The liquid medium may be the same as the solvent in the reaction mixture. In addition, the liquid medium may be water, C5-C10 alcohol, C2-C6 diol, C3-C6 triol, a polymer thereof, or a mixture thereof.

Since the inlet of the reaction vessel is connected to a channel through which a fluid may flow, the sample or solvent may be continuously introduced. Accordingly, CBD may be continuously produced by continuously passing the reaction mixture from the inlet and out through the outlet and irradiating microwaves during passing.

Therefore, the reactor vessel may be connected to the temperature controller. The reaction vessel may be connected while passing through the temperature controller, and the temperature controller may include a temperature control chamber capable of containing a liquid. The temperature control chamber may include a microwave-transparent material. The temperature control chamber may have microwave transparency.

The reaction vessel may be connected to a microwave generator so that microwaves may be irradiated to the reaction mixture therein. The microwave generator may be, for example, commercially available. The microwave generator may be, for example, a microwave reactor manufactured by CEM (model no. 908005). The reaction vessel may include a channel which is connected to the inlet and the outlet such that a fluid flows therethrough. The channel is connected to a pump to control fluid flow.

The reaction vessel may also be connected to a detector for detecting a substance. The detector may include an infrared (IR) sensor, HPLC, MS, etc.

In the method, the *Cannabis* sp. plant may include *Cannabis* sp., such as *Cannabis chemovars, Cannabis sativa, Cannabis indica, Cannabis ruderalis*, etc., wild sp. thereof, variants thereof, mutants thereof, hybrids thereof, and plants including cannabinoid, etc. Further, the *Cannabis* sp. plant may be a living plant or a dried or non-dried plant. Further, the *Cannabis* sp. plant may be leaves, flower buds, fruits, trichomes, flower bracts, stems, roots, or any part including cannabinoids. Further, the *Cannabis* sp. plant may be a dioecious plant, and its cannabinoid content may vary depending on female and male plants. The *Cannabis* sp. plant may be a female plant, a male plant, or a mixture thereof.

In the method, the extract may be obtained by a method including contacting any solvent with the *Cannabis* sp. plant. The solvent may be a solvent capable of extracting or dissolving cannabinoid, for example, CBDA in the *Cannabis* sp. plant. The solvent may be water, a protonic solvent, an aprotonic solvent, or a mixture thereof. The protonic solvent may be C1-C6 alcohol or C1-C4 alcohol. The aprotonic solvent may be C3-C10 ester, C3-C10 ketone, or unsubstituted or halogenated C1-C6 hydrocarbon. The extract may have an increased total content of CBDA and CBD which are cannabinoids.

The total content of CBDA and CBD which are cannabinoids in the extract may be 1% or more, or 5% or more, for example, 1% to 90%, 5% to 90%, 5% to 80%, 5% to 70%, 5% to 60%, 5% to 50%, 5% to 40%, 5% to 30%, 5% to 20%, 5% to 10%, 5% to 9%, 5% to 8%, 5% to 7%, or 5% to 6%, based on the weight of the extract. The extract has no phase separation when concentrated, and may have high solubility.

In the method, the extract may be obtained by a method including incubating a reaction mixture including cannabinoids and a solvent, for example, a protonic solvent. The incubating may be performed at 20° C. to a reflux temperature of a single solvent or a mixed solvent used, 25° C. to a reflux temperature of a single solvent or a mixed solvent used, 30° C. to a reflux temperature of a single solvent or a mixed solvent used, or 35° C. to a reflux temperature of a single solvent or a mixed solvent used.

In the method, the protonic solvent may be ethanol, n-propanol, isopropanol, n-butanol, a mixture thereof, or an aqueous solution thereof.

In the method, the extract may be obtained by a method including incubating a reaction mixture including cannabinoids and a solvent, for example, an aprotonic solvent. The incubating may be performed at 20° C. to a reflux temperature of a single solvent or a mixed solvent used, 25° C. to a reflux temperature of a single solvent or a mixed solvent used, 30° C. to a reflux temperature of a single solvent or a mixed solvent used, or 35° C. to a reflux temperature of a single solvent or a mixed solvent used.

In the method, the aprotonic solvent may be ethyl acetate, acetone, 2-butanone, chloroform, dichloromethane, hexane, or a mixture thereof.

In the method, the *Cannabis* sp. plant may be leaves, flower buds, fruits, trichomes, flower bracts, stems, roots, or any part including cannabinoids.

In the method, the content of CBDA and CBD in the extract may be 1% or more, or 5% or more, for example, 1% to 90%, 5% to 90%, 5% to 80%, 5% to 70%, 5% to 60%, 5% to 50%, 5% to 40%, 5% to 30%, 5% to 20%, 5% to 10%, 5% to 9%, 5% to 8%, 5% to 7%, or 5% to 6%, based on the total weight of the extract.

Conversion of CBDA included in the cannabis plant or the extract thereof into CBD through a decarboxylation reaction may be achieved by microwave irradiation.

In the method, an appropriate temperature of the microwave irradiation may be selected according to the solvent, the content of CBD in a final product, or a ratio of CBD to CBDA. The microwave irradiation may be carried out at 60° C. to 150° C., for example, 60° C. to 140° C., 60° C. to 130° C., 60° C. to 120° C., 60° C. to 110° C., 60° C. to 100° C., 60° C. to 90° C., 60° C. to 80° C., 60° C. to 70° C., 70° C. to 140° C., 70° C. to 130° C., 70° C. to 120° C., 70° C. to 110° C., 70° C. to 100° C., 70° C. to 90° C., 70° C. to 80° C., 80° C. to 140° C., 80° C. to 130° C., 80° C. to 120° C., 80° C. to 110° C., 80° C. to 100° C., 80° C. to 90° C., 90° C. to 140° C., 90° C. to 130° C., 90° C. to 120° C., 90° C. to 110° C., 90° C. to 100° C., 100° C. to 140° C., 100° C.

to 130° C., 100° C. to 120° C., 100° C. to 110° C., 110° C. to 140° C., 110° C. to 130° C., 110° C. to 120° C., 120° C. to 140° C., 120° C. to 130° C., or 130° C. to 140° C.

In the method, the microwave irradiation may be carried out for a time sufficient to convert CBDA to CBD. The microwave irradiation may be carried out for a time sufficient to convert CBDA to CBD while retaining the reaction mixture in the vessel. The retention time may be controlled by the pump. Further, the retention time may be controlled by controlling the flow rate according to a ratio between the length in the flow direction and the height of the vessel.

The microwave irradiation time may vary depending on the thickness and length of the tube, the reaction temperature, a microwave output power, the solvent used, and use of the final product. As used herein, the "microwave irradiation time" refers to the time for which microwaves are irradiated to the reaction mixture, independent of an operating time of the microwave generator. The microwave irradiation time represents the time for which the reactants are exposed to microwaves while flowing through the tube in the reactor. Therefore, even though the microwave generator is turned on, if the reactants are not exposed to microwaves, it is not included in the microwave irradiation time. The microwave irradiation time becomes longer as the flow rate is slower. The microwave irradiation time may be 5 min to 180 min, for example, 10 min to 180 min, 10 min to 150 min, 10 min to 100 min, 10 min to 90 min, 20 min to 180 min, 20 min to 150 min, 20 min to 100 min, 20 min to 90 min, 30 min to 180 min, 30 min to 150 min, 30 min to 100 min, 30 min to 90 min, 5 min to 30 min, 5 min to 20 min, 5 min to 10 min, 10 min to 30 min, 10 min to 20 min, or 20 min to 30 min.

In the method, the microwave irradiation may be carried out while passing the reaction mixture via the pump at a flow rate of 0.010 mL to 10 mL per min. The flow rate may be, for example, 0.010 mL to 5.0 mL per min, 0.010 mL to 2.0 mL per min, 0.010 mL to 1.0 mL per min, 0.010 mL to 0.50 mL per min, 0.010 mL to 0.10 mL per min, 0.10 mL to 10 mL per min, 0.10 mL to 5.0 mL per min, 0.10 mL to 2.0 mL per min, 0.10 mL to 1.0 mL per min, 0.10 mL to 0.50 mL per min, 0.50 mL to 10 mL per min, 0.50 mL to 5.0 mL per min, 0.50 mL to 2.0 mL per min, 0.50 mL to 1.0 mL per min, 1.0 mL to 10 mL per min, 1.0 mL to 5.0 mL per min, 1.0 mL to 2.0 mL per min, 2.0 mL to 10 mL per min, 2.0 mL to 5.0 mL per min, or 5.0 mL to 10 mL per min.

In the method, the microwave irradiation may be carried out under pressure. The microwave irradiation may be carried out under a pressure of more than 1 atm to 100 atm, for example, 2 atm to 100 atm, 2 atm to 50 atm, 2 atm to 30 atm, 2 atm to 20 atm, or 2 atm to 15 atm.

In the microwave irradiation of the method, the microwave output power may be 3 W to 6 kW, for example, 10 W to 6 kW, 10 W to 3 kW, 10 W to 1 kW, 10 W to 500 W, 10 W to 100 W, 10 W to 70 W, 10 W to 50 W, or 3 W to 50 W.

In the method, the microwave irradiation indicates a thermal reaction of heating the cannabis plant or the extract thereof by irradiating microwaves thereto. The microwave may be microwave having a frequency of 300 MHz to 300 GHz, for example, 1000 MHz to 100 GHz, 1000 MHz to 50 GHz, 1000 MHz to 10 GHz, or 1000 MHz to 5 GHz. In a specific embodiment, the microwave irradiation may be carried at 500 MHz to 5000 MHz, 500 MHz to 4000 MHz, 1000 MHz to 5000 MHz, 1000 MHz to 3000 MHz, 2000 MHz to 4000 MHz, or 2000 MHz to 3000 MHz.

In the method, the produced or isolated cannabinoid may be CBD.

In the microwave irradiation of the method, the solvent may be C1-C12 alcohol or an aqueous solution thereof, for example, ethanol, isopropanol, butanol, a mixture thereof, or an aqueous solution thereof. The aqueous solution may be a 50% to 99% ethanol aqueous solution. The C1-C12 alcohol may be C1-C6 alcohol, C1-C4 alcohol, or C2-C5 alcohol.

The microwave irradiation may be carried out to convert 10% to 100%, for example, 20% to 100%, 25% to 100%, 30% to 100%, 50% to 100%, 80% to 100%, 90% to 100%, 95% to 100%, 97% to 100%, or 100% of the CBDA ingredient included in the *Cannabis* sp. plant or the extract thereof into the CBD ingredient.

The reaction mixture may include CBDA dissolved in the solvent. The CBDA may be included at a concentration of 1 ppm to a saturation concentration of CBDA for the corresponding solvent, 10 ppm to a saturation concentration of CBDA for the corresponding solvent, 50 ppm to a saturation concentration of CBDA for the corresponding solvent, 100 ppm to a saturation concentration of CBDA for the corresponding solvent, 200 ppm to a saturation concentration of CBDA for the corresponding solvent, 200 ppm to 10,000 ppm, 200 ppm to 5,000 ppm, 500 ppm to 10,000 ppm, 500 ppm to 5,000 ppm, or 500 ppm to 1,000 ppm.

The reaction mixture may include a cannabis extract including CBDA dissolved in the solvent. The extract may be included at a concentration of 1 ppm to a saturation concentration of the extract for the corresponding solvent, 10 ppm to a saturation concentration of the extract for the corresponding solvent, 50 ppm to a saturation concentration of the extract for the corresponding solvent, 100 ppm to a saturation concentration of the extract for the corresponding solvent, 200 ppm to a saturation concentration of the extract for the corresponding solvent, 200 ppm to 10,000 ppm, 200 ppm to 5,000 ppm, 500 ppm to 10,000 ppm, 500 ppm to 5,000 ppm, or 500 ppm to 1,000 ppm.

In the method, the isolated cannabinoid may include 10% by weight to 100% by weight, for example, 10% by weight to 99% by weight, 10% by weight to 95% by weight, 10% by weight to 90% by weight, 20% by weight to 100% by weight, 20% by weight to 99% by weight, 20% by weight to 95% by weight, or 20% by weight to 90% by weight of CBD, based on the total weight of the isolate.

The method may include isolating cannabinoid from the microwave-irradiated reaction mixture. The isolating may be isolating CBD.

The isolating may include performing chromatography of the microwave-irradiated reaction mixture. The chromatography may be, for example, reverse-phase C18 column chromatography or reverse-phase semi-preparative high performance liquid chromatography. As a result, the reaction mixture may be a polar fraction of the solvent by silica gel, and a mixture with a high content of CBD or a single ingredient of CBD by isolation through preparative liquid chromatography may be obtained.

The isolation method by reverse-phase C18 column chromatography is an isolation method commonly used in a laboratory. Depending on the amount of a sample to be separated, a diameter of a glass column to be used and the amount of reverse-phase C18 to be used may vary. Generally, in the case of the glass column, a column having an internal diameter of 1 cm to 10 cm and a length of 10 cm to 100 cm, in which 50% to 70% of the height of the column is packed with reversed phase C18, may be used. A composition of an eluent to be used slightly varies depending on the amount of the sample and the silica gel column. For example, a mixed solvent having a volume ratio of methanol:water:ethyl acetate=1:1:0 to 1:0:0 to 0:0:1 may be sequentially used according to the mixing ratio.

The isolation conditions by reverse-phase semi-preparative HPLC may vary depending on the amount of the sample and the size of a column to be used. Generally, reverse-phase preparative HPLC (stationary phase: Luna C18(2) column, Phenomenex, particle size of 10 μm, length of 250 mm×10 mm) is prepared in a liquid chromatography (Shimadzu) instrument, and the sample dissolved in an initial eluent is injected, and then isolation may be performed while developing the eluent from acetonitrile:water=50:50 (v/v) to acetonitrile:water=100:0 (v/v) for 60 min to 90 min.

Another aspect provides an antiepileptic, neuroprotective, vasorelaxant, anti-cancer, anti-inflammatory, anti-diabetic, anti-bacterial, analgesic, anti-osteoporosis, immune-enhancing, or antiemetic pharmaceutical composition, the pharmaceutical composition including, as an active ingredient, the cannabinoid isolated by the above method. The cannabinoid may be CBD. The cannabinoid may be a fraction, a single compound, or a mixture thereof. The pharmaceutical composition may further include a pharmaceutically acceptable carrier or diluent.

The cannabinoid has improved CBD efficacy due to a significantly high content of CBD, as compared with a processed product resulting from simple heat-treatment. CBD is known to have antiepileptic, neuroprotective, vasorelaxant, anti-cancer, anti-inflammatory, anti-diabetic, anti-bacterial, analgesic, anti-osteoporosis, immune-enhancing, or antiemetic effects. Therefore, these effects may be significantly increased by the microwave irradiation, as compared with a processed product resulting from simple heat-treatment.

Still another aspect provides a health functional food composition including, as an active ingredient, the cannabinoid isolated by the above method. The cannabinoid may be CBD. The cannabinoid may be a fraction, a single compound, or a mixture thereof. The food may be a functional food or a health functional food. The functional ingredient of the food is a safe food composition partially including the pharmaceutical ingredient, and may further include a carrier or diluent acceptable for use in foods.

Still another aspect provides a cosmetic composition including, as an active ingredient, the cannabinoid isolated by the above method. The cosmetics may be general cosmetics or functional cosmetics. CBD, known as a functional ingredient of cosmetics, may be a composition having an antioxidant or anti-inflammatory effect. The cosmetic composition may further include a carrier or diluent acceptable for use in cosmetics.

Still another aspect provides a method of treating a disease of an individual, the method including administering, to the individual, a composition including, as an active ingredient, the cannabinoid isolated by the above method. The disease may be a disease in need of antiepileptic, neuroprotective, vasorelaxant, anti-cancer, anti-inflammatory, anti-diabetic, anti-bacterial, analgesic, anti-osteoporosis, immune-enhancing, or antiemetic effects.

Still another aspect provides a method of putting on make-up, the method including applying, to an individual, a composition including, as an active ingredient, the cannabinoid isolated by the above method.

BRIEF DESCRIPTION OF THE DRAWINGS

The above and other aspects, features, and advantages of certain embodiments of the disclosure will be more apparent from the following description taken in conjunction with the accompanying drawings, in which.

DETAILED DESCRIPTION

Figure 1:
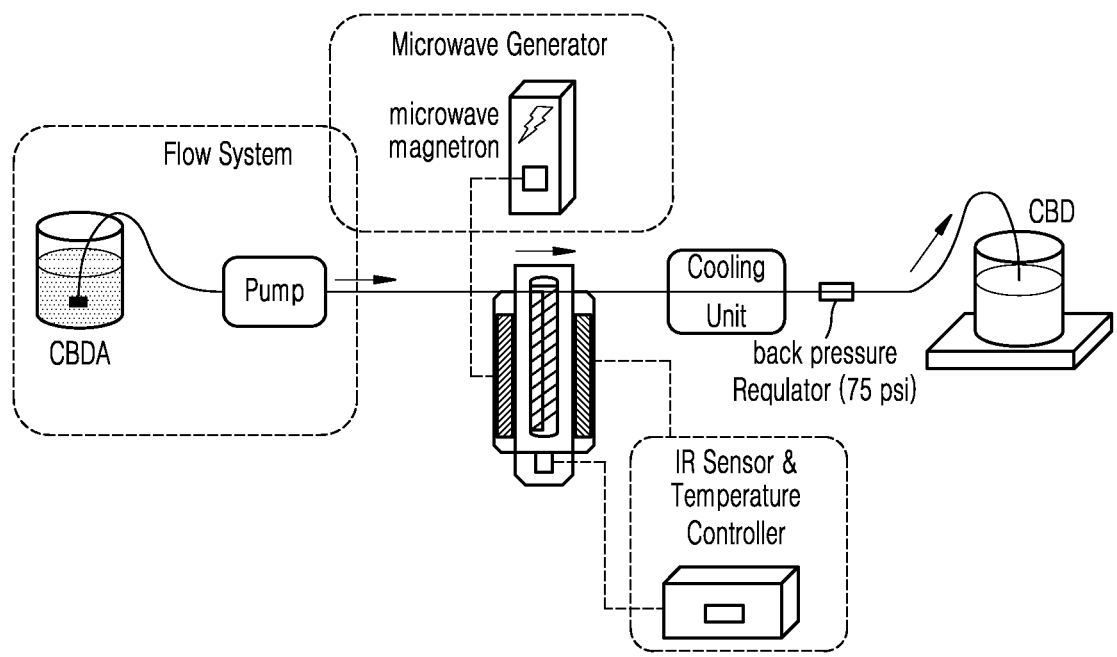
FIG. 1 shows an illustration of continuous microwave processing equipment.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

Hereinafter, the present disclosure will be described in more detail with reference to exemplary embodiments. However, these exemplary embodiments are only for illustrating the present disclosure, and the scope of the present disclosure is not limited to these exemplary embodiments.

Example 1: Preparation of Cannabis Extract

Cannabis used in the present Examples was deposited by JayHempKorea Ltd., located in Sangju city, Gyeongsangbuk-do, South Korea, through assignment/transfer approval processes under drug (cannabis) research permission (No. 1564) obtained from the Ministry of Food and Drug Safety and Seoul Regional Food and Drug Administration. Cannabis seed skins, cannabis leaves, cannabis stems, and cannabis roots were harvested in October, 2018, and used after being finely cut. 200 g of finely cut cannabis leaves having a relatively high content of cannabinoids among the parts of cannabis and 2.0 L of ethyl acetate were added to in a 5.0 L Erlenmeyer flask, and microwave-irradiated using an ultrasonic processor (Sonics, VC505) at 40% power of the instrument for 1 hr, i.e., 200 W, and then incubated at room temperature for 24 hr. This procedure was repeated twice.

The liquid extract, which was obtained by filtering the microwave-irradiated mixture of the finely cut cannabis leaves and ethyl acetate through a filter, was concentrated by evaporation under reduced pressure to obtain 17.6 g of a cannabis leave extract including CBDA and CBD.

Example 2: Manufacture of Continuous Microwave Processing Equipment

As a continuous microwave processing equipment, a microwave irradiator (model no. 908005) manufactured by CEM Company (USA) was used, and a tube made of PTFE and PFA was inserted into a reaction chamber of a 10-mL flow cell accessory (model no. 908910) to manufacture a continuous reactor. Thereafter, the chamber of the continuous reactor was filled with water, and a liquid-feeding pump (YMC-KP series) was connected to one end of the inserted tube, i.e., to a tube at an inlet through which the reaction mixture is applied, and a back pressure regulator of 75 psi (UPCHURCH, P-786) was connected to the other end, i.e., to a tube at an outlet through which the reaction mixture is discharged. The tube had an outer diameter (O. D.) of $1/16$ inch, an inner diameter (I. D.) of 1.0 mm, a length of 127.4 cm, and an inner tube volume of 1.0 mL. A volume of the chamber containing the tube was 10 mL. The chamber acts as a temperature controller by transferring heat of water filled therein to the tube.

FIG. 1 shows an illustration of continuous microwave processing equipment.

Examples 3 to 25: Continuous Microwave Processing of Cannabis Leaf Extract

The ethyl acetate extract obtained in Example 1 was subjected to continuous microwave processing. In detail, the cannabis extract was dissolved at a concentration of 200 ppm in ethanol, and then a reaction temperature of the continuous reactor was set at 70° C., and continuous microwave processing was carried out at a microwave maximum power of 45 W and a frequency of 2450 MHz for 10 min (Example 3) and 20 min (Example 4). Microwaves were irradiated in such a manner at 80° C. for 10 min (Example 5), 20 min (Example 6), 40 min (Example 7), and 60 min (Example 8), at 90° C. for 10 min (Example 9), 20 min (Example 10), 30 min (Example 11), 40 min (Example 12), and 60 min (Example 13), and at 100° C. for 5 min (Example 14) and 10 min (Example 15) to obtain microwave-irradiated process products, respectively. Next, a reaction temperature of the continuous reactor was set at 90° C. and 30 min, and microwaves were irradiated using, as solvents, butanol (Example 16), isopropanol (Example 17), an 80% ethanol aqueous solution (Example 18), ethyl acetate (Example 19), acetonitrile (Example 20), acetone (Example 21), hexane (Example 22) and 1,2-dichloroethane (Example 23) to obtain processed products, respectively. Next, the cannabis extract was dissolved at a concentration of 10,000 ppm in ethanol, and then microwaves were irradiated for 30 min at 90° C. (Example 24) and at 95° C. (Example 25) to obtain processed products, respectively.

Each reaction time was controlled by controlling the flow rate of the liquid-feeding pump, and the power was 3 W to 45 W during microwave irradiation, and the content analysis was performed according to an analysis method of Experimental Example 1. The reaction time according to the flow rate is as follows: 5 min at 0.2 mL/min, 10 min at 0.1 mL/min, 20 min at 0.05 mL/min and 30 min at 0.033 mL/min, 40 min at 0.025 mL/min, and 60 min at 0.017 mL/min. Here, the reaction time represents the time for which the reactants remain in the tube in the continuous reactor. During the microwave irradiation, the power may vary depending on the size of the inner diameter of the tube.

Experimental Example 1: Analysis of Cannabinoids in Extracts and Continuous Microwave-Processed Products

(1) Experimental Method

Based on values of CBDA and CBD calibration curves, cannabinoids in the cannabis extracts and the processed extracts obtained in Examples were analyzed, and repeated in triplicate to confirm reproducibility. As for CBDA and CBD single ingredients used in the experiments, CBDA with purity of 97.1% and CBD with purity of 96.3% directly isolated from the cannabis leaf raw material were used. According to the general calibration curve analysis method, CBDA and CBD were dissolved in water at 10 ppm, 25 ppm, 50 ppm, 100 ppm, and 250 ppm to prepare standard solutions, respectively, which were used to construct calibration curves. An elution solvent A and an elution solvent B used in ultra-performance liquid chromatography (UPLC) were water and acetonitrile, respectively, and each was pumped using two pumps. 3 μl of the standard aqueous solution was injected into a reverse-phase column for analysis (Phenomenex Luna Omega 1.6μ Polar C18, 150 mm×2.1 mm) using a syringe, and an elution solvent consisting of 70% by volume of A and 30% by volume of B was applied at a flow rate of 0.3 mL/min. Thereafter, % volume of the elution solvent B were gradually changed to 100% (20 min), 100% (23 min), and 30% (26 min). After the above procedures, each ingredient isolated from the column was analyzed by UV spectrum.

(2) Experimental Results

As a result of the experiments, each ingredient isolated from the column was analyzed by UPLC analysis of the cannabis leaf extracts, and peaks of FIGS. 4 to 27 were obtained by the analysis results of UPLC chromatograms.

Figure 2:
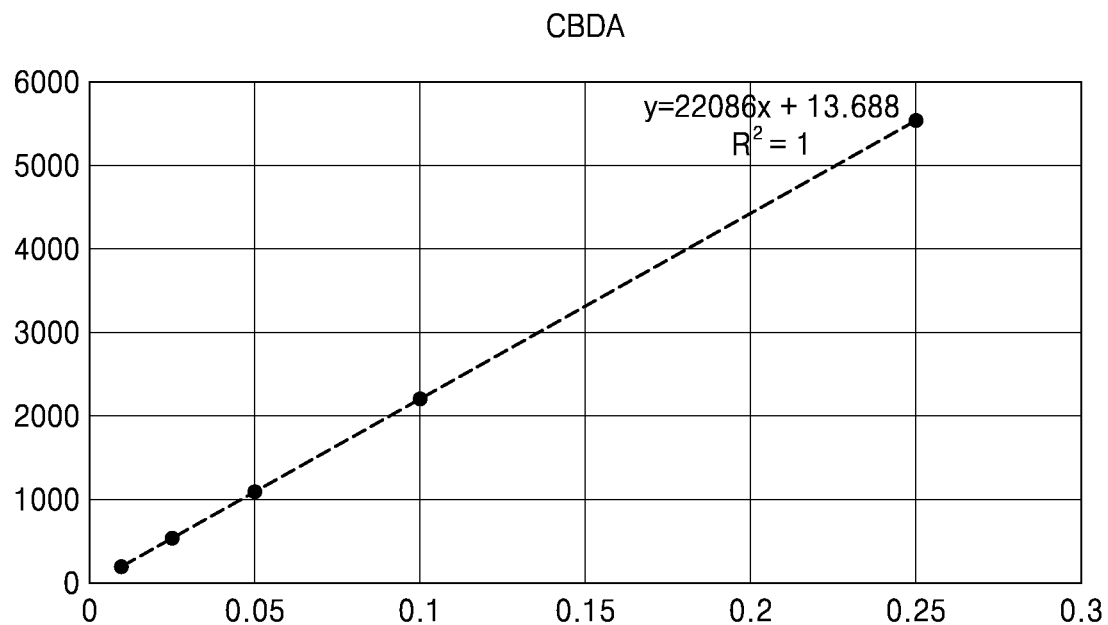
FIG. 2 shows a calibration curve constructed by analyzing CBDA according to concentration.

FIG. 2 shows a calibration curve constructed by analyzing CBDA according to concentration.

Figure 3:
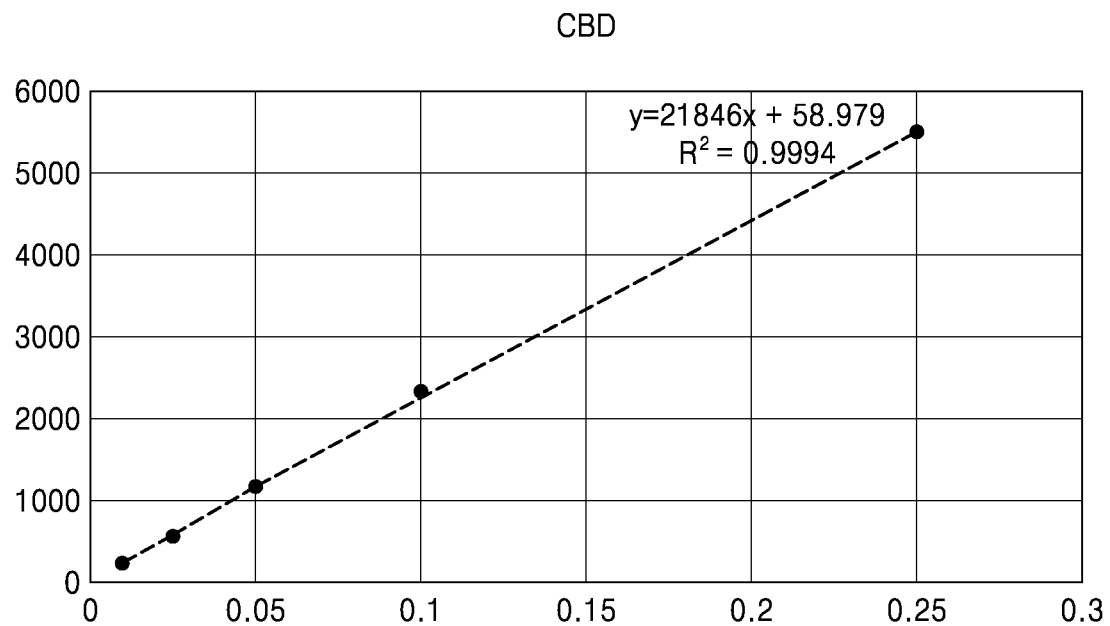
FIG. 3 shows a calibration curve constructed by analyzing CBD according to concentration.

FIG. 3 shows a calibration curve constructed by analyzing CBD according to concentration.

Figure 4:
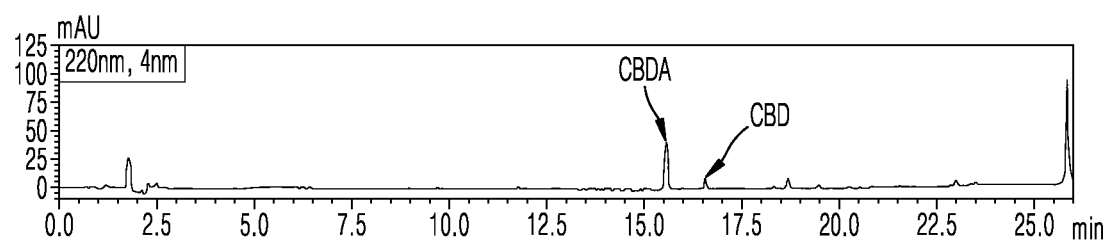
FIG. 4 shows a UPLC chromatogram for analyzing cannabinoid ingredients in an extract of a raw material cannabis leaf, hereinbelow, the "extract of the raw material cannabis leaf" indicates an extract obtained in Example 1 by extraction with an ethyl acetate solvent.

FIG. 4 shows a UPLC chromatogram for analyzing cannabinoid ingredients in an extract of a raw material cannabis leaf. UPLC chromatogram for analyzing a 200 ppm solution of the extract of cannabis leaves in ethanol, which was obtained in Example 1, is shown.

Figure 5:
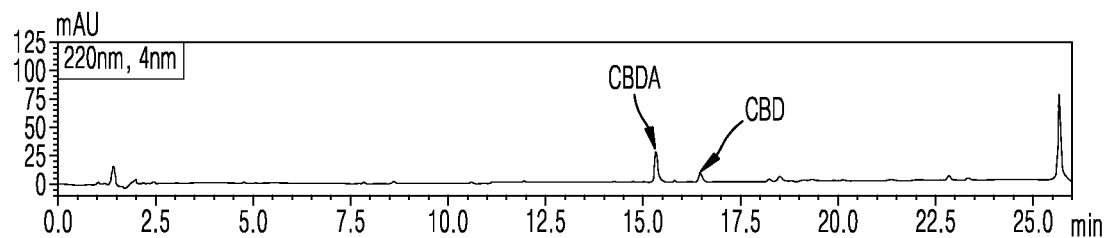
FIG. 5 shows a UPLC chromatogram for analyzing cannabinoid ingredients in a processed product obtained by microwave-irradiation for 10 minutes while applying a 200 ppm solution of the extract of cannabis leaves in ethanol to a tube with a volume of 1.0 mL through a liquid-feeding pump at 70° C. at a flow rate of 0.10 mL/min.

FIG. 5 shows a UPLC chromatogram for analyzing cannabinoid ingredients in a processed product obtained by microwave-irradiation for 10 min while applying a 200 ppm solution of the extract of cannabis leaves in ethanol to a tube with a volume of 1.0 mL through a liquid-feeding pump at 70° C. at a flow rate of 0.10 mL/min.

Figure 6:
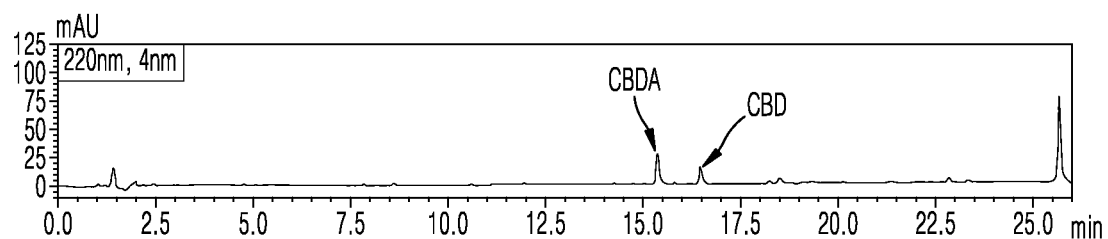
FIG. 6 shows a UPLC chromatogram for analyzing cannabinoid ingredients in a processed product obtained by microwave-irradiation for 20 minutes while applying a 200 ppm solution of the extract of cannabis leaves in ethanol to a tube with a volume of 1.0 mL through a liquid-feeding pump at 70° C. at a flow rate of 0.05 mL/min.

FIG. 6 shows a UPLC chromatogram for analyzing cannabinoid ingredients in a processed product obtained by microwave-irradiation for 20 min while applying a 200 ppm solution of the extract of cannabis leaves in ethanol to a tube with a volume of 1.0 mL through a liquid-feeding pump at 70° C. at a flow rate of 0.05 mL/min.

Figure 7:
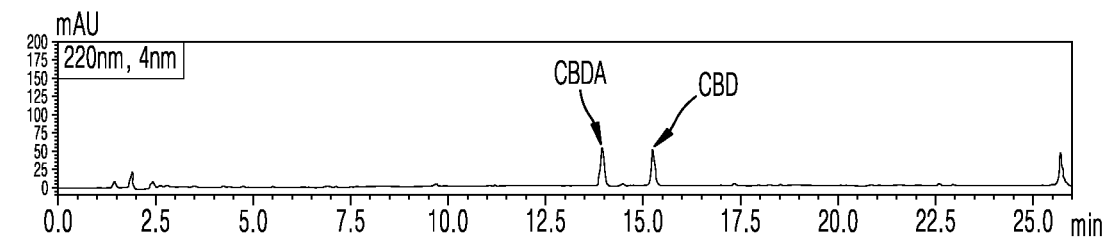
FIG. 7 shows a UPLC chromatogram for analyzing cannabinoid ingredients in a processed product obtained by microwave-irradiation for 10 minutes while applying a 200 ppm solution of the extract of cannabis leaves in ethanol to a tube with a volume of 1.0 mL through a liquid-feeding pump at 80° C. at a flow rate of 0.10 mL/min.

FIG. 7 shows a UPLC chromatogram for analyzing cannabinoid ingredients in a processed product obtained by microwave-irradiation for 10 min while applying a 200 ppm solution of the extract of cannabis leaves in ethanol to a tube with a volume of 1.0 mL through a liquid-feeding pump at 80° C. at a flow rate of 0.10 mL/min.

Figure 8:
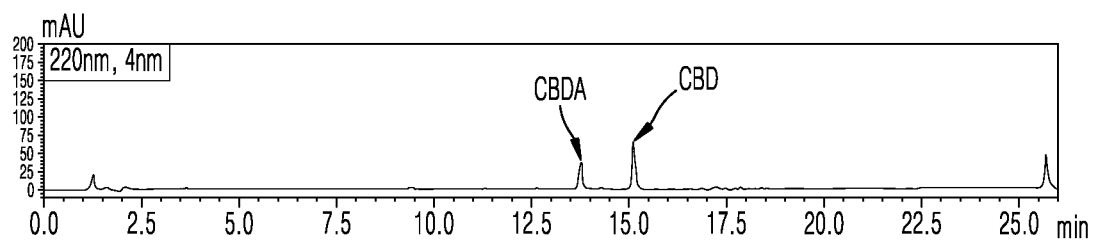
FIG. 8 shows a UPLC chromatogram for analyzing cannabinoid ingredients in a processed product obtained by microwave-irradiation for 20 minutes while applying a 200 ppm solution of the extract of cannabis leaves in ethanol to a tube with a volume of 1.0 mL through a liquid-feeding pump at 80° C. at a flow rate of 0.05 mL/min.

FIG. 8 shows a UPLC chromatogram for analyzing cannabinoid ingredients in a processed product obtained by microwave-irradiation for 20 min while applying a 200 ppm solution of the extract of cannabis leaves in ethanol to a tube with a volume of 1.0 mL through a liquid-feeding pump at 80° C. at a flow rate of 0.05 mL/min.

Figure 9:
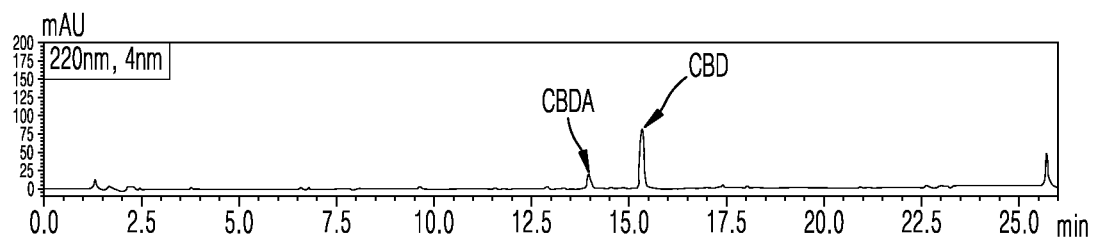
FIG. 9 shows a UPLC chromatogram for analyzing cannabinoid ingredients in a processed product obtained by microwave-irradiation for 40 minutes while applying a 200 ppm solution of the extract of cannabis leaves in ethanol to a tube with a volume of 1.0 mL through a liquid-feeding pump at 80° C. at a flow rate of 0.025 mL/min.

FIG. 9 shows a UPLC chromatogram for analyzing cannabinoid ingredients in a processed product obtained by microwave-irradiation for 40 min while applying a 200 ppm solution of the extract of cannabis leaves in ethanol to a tube with a volume of 1.0 mL through a liquid-feeding pump at 80° C. at a flow rate of 0.025 mL/min.

Figure 10:
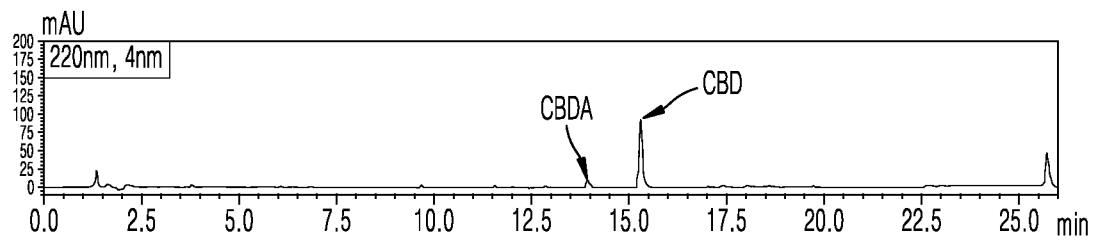
FIG. 10 shows a UPLC chromatogram for analyzing cannabinoid ingredients in a processed product obtained by microwave-irradiation for 60 minutes while applying a 200 ppm solution of the extract of cannabis leaves in ethanol to a tube with a volume of 1.0 mL through a liquid-feeding pump at 80° C. at a flow rate of 0.017 mL/min.

FIG. 10 shows a UPLC chromatogram for analyzing cannabinoid ingredients in a processed product obtained by microwave-irradiation for 60 min while applying a 200 ppm solution of the extract of cannabis leaves in ethanol to a tube with a volume of 1.0 mL through a liquid-feeding pump at 80° C. at a flow rate of 0.017 mL/min.

Figure 11:
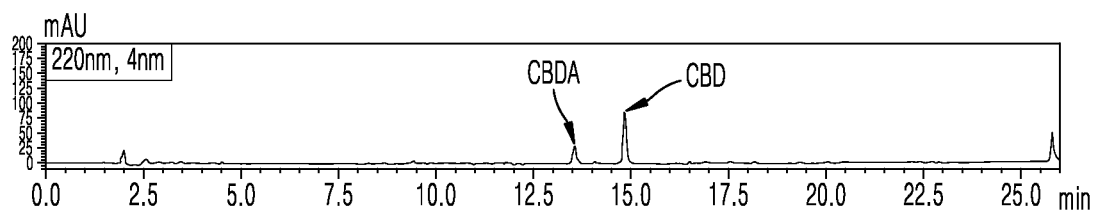
FIG. 11 shows a UPLC chromatogram for analyzing cannabinoid ingredients in a processed product obtained by microwave-irradiation for 10 minutes while applying a 200 ppm solution of the extract of cannabis leaves in ethanol to a tube with a volume of 1.0 mL through a liquid-feeding pump at 90° C. at a flow rate of 0.10 mL/min.

FIG. 11 shows a UPLC chromatogram for analyzing cannabinoid ingredients in a processed product obtained by microwave-irradiation for 10 min while applying a 200 ppm solution of the extract of cannabis leaves in ethanol to a tube with a volume of 1.0 mL through a liquid-feeding pump at 90° C. at a flow rate of 0.10 mL/min.

Figure 12:
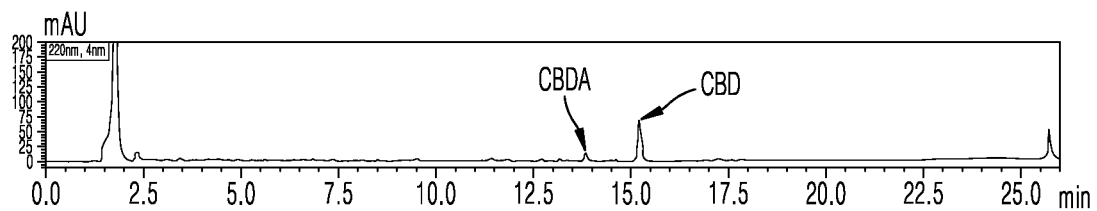
FIG. 12 shows a UPLC chromatogram for analyzing cannabinoid ingredients in a processed product obtained by microwave-irradiation for 20 min while applying a 200 ppm solution of the extract of cannabis leaves in ethanol to a tube with a volume of 1.0 mL through a liquid-feeding pump at 90° C. at a flow rate of 0.05 mL/min.

FIG. 12 shows a UPLC chromatogram for analyzing cannabinoid ingredients in a processed product obtained by microwave-irradiation for 20 min while applying a 200 ppm solution of the extract of cannabis leaves in ethanol to a tube with a volume of 1.0 mL through a liquid-feeding pump at 90° C. at a flow rate of 0.05 mL/min.

Figure 13:
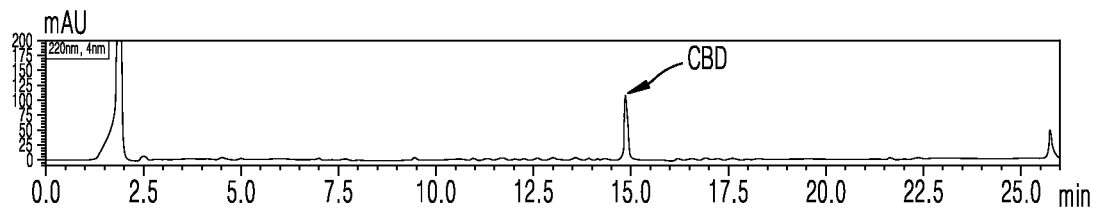
FIG. 13 shows a UPLC chromatogram for analyzing cannabinoid ingredients in a processed product obtained by microwave-irradiation for 30 minutes while applying a 200 ppm solution of the extract of cannabis leaves in ethanol to a tube with a volume of 1.0 mL through a liquid-feeding pump at 90° C. at a flow rate of 0.033 mL/min.

FIG. 13 shows a UPLC chromatogram for analyzing cannabinoid ingredients in a processed product obtained by microwave-irradiation for 30 min while applying a 200 ppm solution of the extract of cannabis leaves in ethanol to a tube with a volume of 1.0 mL through a liquid-feeding pump at 90° C. at a flow rate of 0.033 mL/min.

Figure 14:
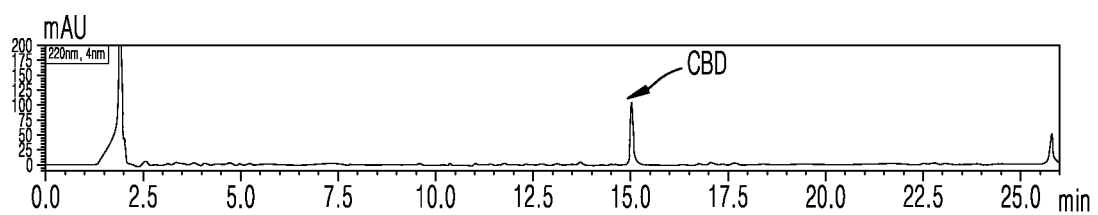
FIG. 14 shows a UPLC chromatogram for analyzing cannabinoid ingredients in a processed product obtained by microwave-irradiation for 40 minutes while applying a 200 ppm solution of the extract of cannabis leaves in ethanol to a tube with a volume of 1.0 mL through a liquid-feeding pump at 90° C. at a flow rate of 0.025 mL/min.

FIG. 14 shows a UPLC chromatogram for analyzing cannabinoid ingredients in a processed product obtained by microwave-irradiation for 40 min while applying a 200 ppm solution of the extract of cannabis leaves in ethanol to a tube with a volume of 1.0 mL through a liquid-feeding pump at 90° C. at a flow rate of 0.025 mL/min.

Figure 15:
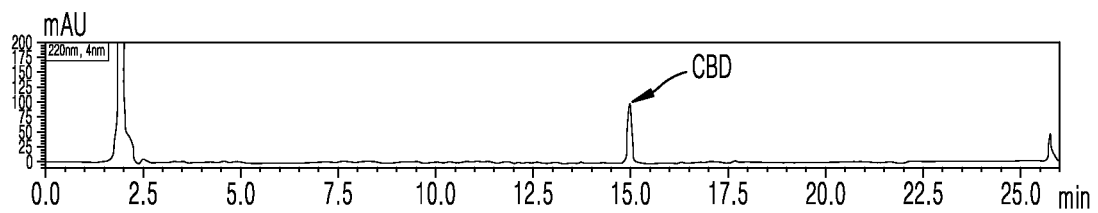
FIG. 15 shows a UPLC chromatogram for analyzing cannabinoid ingredients in a processed product obtained by microwave-irradiation for 60 minutes while applying a 200 ppm solution of the extract of cannabis leaves in ethanol to a tube with a volume of 1.0 mL through a liquid-feeding pump at 90° C. at a flow rate of 0.017 mL/min.

FIG. 15 shows a UPLC chromatogram for analyzing cannabinoid ingredients in a processed product obtained by microwave-irradiation for 60 min while applying a 200 ppm solution of the extract of cannabis leaves in ethanol to a tube with a volume of 1.0 mL through a liquid-feeding pump at 90° C. at a flow rate of 0.017 mL/min.

Figure 16:
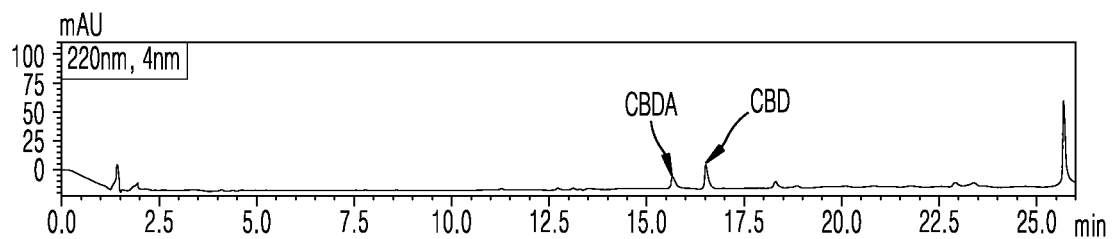
FIG. 16 shows a UPLC chromatogram for analyzing cannabinoid ingredients in a processed product obtained by microwave-irradiation for 5 minutes while applying a 200 ppm solution of the extract of cannabis leaves in ethanol to a tube with a volume of 1.0 mL through a liquid-feeding pump at 100° C. at a flow rate of 0.20 mL/min.

FIG. 16 shows a UPLC chromatogram for analyzing cannabinoid ingredients in a processed product obtained by microwave-irradiation for 5 min while applying a 200 ppm solution of the extract of cannabis leaves in ethanol to a tube with a volume of 1.0 mL through a liquid-feeding pump at 100° C. at a flow rate of 0.20 mL/min.

Figure 17:
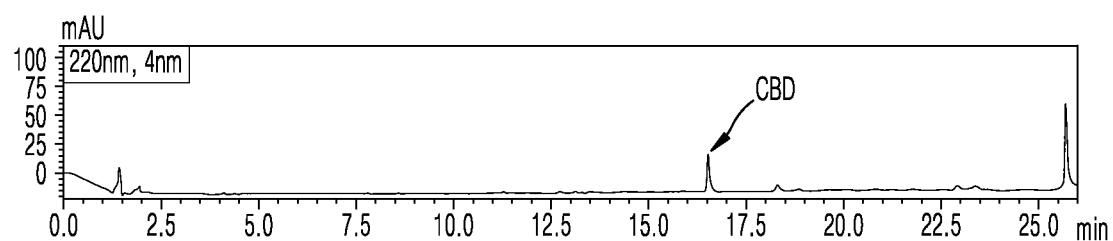
FIG. 17 shows a UPLC chromatogram for analyzing cannabinoid ingredients in a processed product obtained by microwave-irradiation for 10 minutes while applying a 200 ppm solution of the extract of cannabis leaves in ethanol to a tube with a volume of 1.0 mL through a liquid-feeding pump at 100° C. at a flow rate of 0.10 mL/min.

FIG. 17 shows a UPLC chromatogram for analyzing cannabinoid ingredients in a processed product obtained by microwave-irradiation for 10 min while applying a 200 ppm solution of the extract of cannabis leaves in ethanol to a tube with a volume of 1.0 mL through a liquid-feeding pump at 100° C. at a flow rate of 0.10 mL/min.

Figure 18:
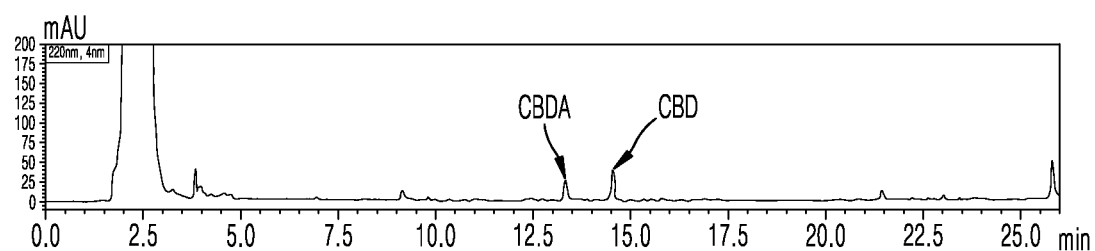
FIG. 18 shows a UPLC chromatogram for analyzing cannabinoid ingredients in a processed product obtained by microwave-irradiation for 30 minutes while applying a 200 ppm solution of the extract of cannabis leaves in butanol to a tube with a volume of 1.0 mL through a liquid-feeding pump at 90° C. at a flow rate of 0.033 mL/min.

FIG. 18 shows a UPLC chromatogram for analyzing cannabinoid ingredients in a processed product obtained by microwave-irradiation for 30 min while applying a 200 ppm solution of the extract of cannabis leaves in butanol to a tube with a volume of 1.0 mL through a liquid-feeding pump at 90° C. at a flow rate of 0.033 mL/min.

Figure 19:
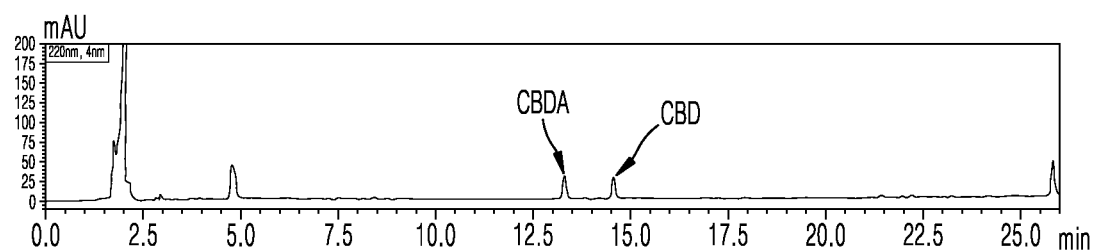
FIG. 19 shows a UPLC chromatogram for analyzing cannabinoid ingredients in a processed product obtained by microwave-irradiation for 30 minutes while applying a 200 ppm solution of the extract of cannabis leaves in isopropanol to a tube with a volume of 1.0 mL through a liquid-feeding pump at 90° C. at a flow rate of 0.033 mL/min.

FIG. 19 shows a UPLC chromatogram for analyzing cannabinoid ingredients in a processed product obtained by microwave-irradiation for 30 min while applying a 200 ppm solution of the extract of cannabis leaves in isopropanol to a tube with a volume of 1.0 mL through a liquid-feeding pump at 90° C. at a flow rate of 0.033 mL/min.

Figure 20:
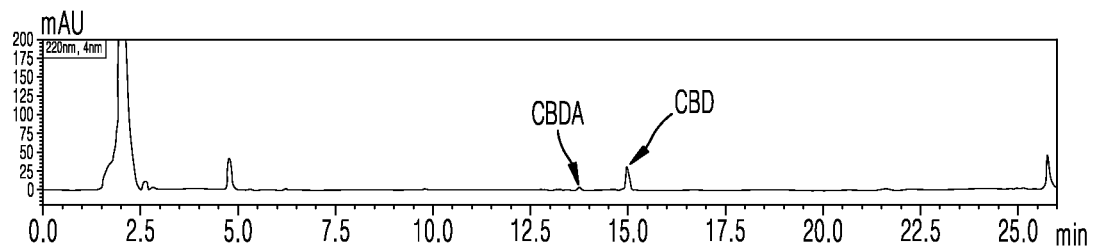
FIG. 20 shows a UPLC chromatogram for analyzing cannabinoid ingredients in a processed product obtained by microwave-irradiation for 30 minutes while applying a 200 ppm solution of the extract of cannabis leaves in an 80% ethanol aqueous solution to a tube with a volume of 1.0 mL through a liquid-feeding pump at 90° C. at a flow rate of 0.033 mL/min.

FIG. 20 shows a UPLC chromatogram for analyzing cannabinoid ingredients in a processed product obtained by microwave-irradiation for 30 min while applying a 200 ppm solution of the extract of cannabis leaves in an 80% ethanol aqueous solution to a tube with a volume of 1.0 mL through a liquid-feeding pump at 90° C. at a flow rate of 0.033 mL/min.

Figure 21:
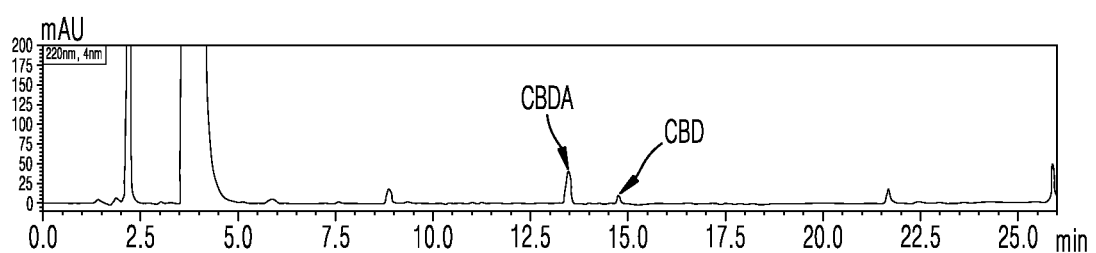
FIG. 21 shows a UPLC chromatogram for analyzing cannabinoid ingredients in a processed product obtained by microwave-irradiation for 30 minutes while applying a 200 ppm solution of the extract of cannabis leaves in ethyl acetate to a tube with a volume of 1.0 mL through a liquid-feeding pump at 90° C. at a flow rate of 0.033 mL/min.

FIG. 21 shows a UPLC chromatogram for analyzing cannabinoid ingredients in a processed product obtained by microwave-irradiation for 30 min while applying a 200 ppm solution of the extract of cannabis leaves in ethyl acetate to a tube with a volume of 1.0 mL through a liquid-feeding pump at 90° C. at a flow rate of 0.033 mL/min.

Figure 22:
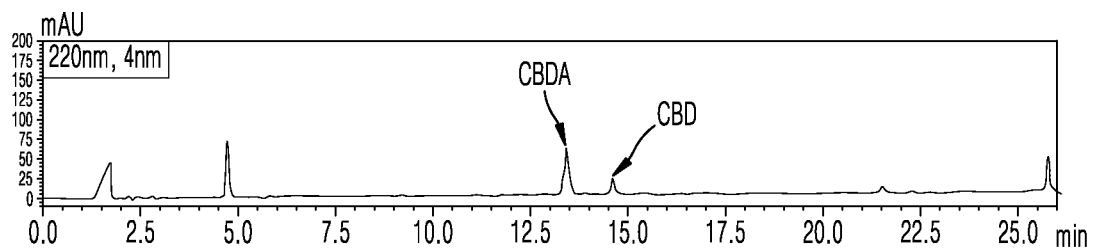
FIG. 22 shows a UPLC chromatogram for analyzing cannabinoid ingredients in a processed product obtained by microwave-irradiation for 30 minutes while applying a 200 ppm solution of the extract of cannabis leaves in acetonitrile to a tube with a volume of 1.0 mL through a liquid-feeding pump at 90° C. at a flow rate of 0.033 mL/min.

FIG. 22 shows a UPLC chromatogram for analyzing cannabinoid ingredients in a processed product obtained by microwave-irradiation for 30 min while applying a 200 ppm solution of the extract of cannabis leaves in acetonitrile to a tube with a volume of 1.0 mL through a liquid-feeding pump at 90° C. at a flow rate of 0.033 mL/min.

Figure 23:
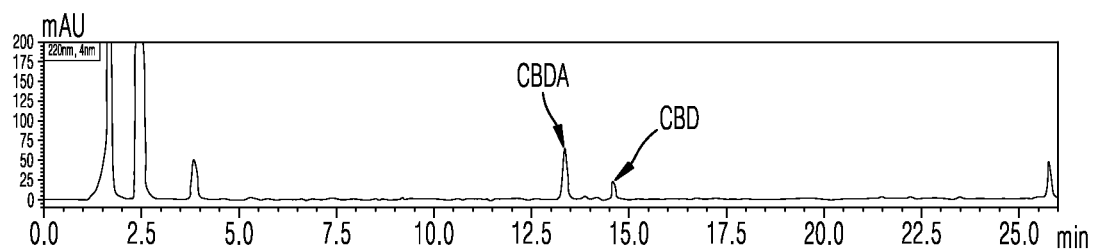
FIG. 23 shows a UPLC chromatogram for analyzing cannabinoid ingredients in a processed product obtained by microwave-irradiation for 30 minutes while applying a 200 ppm solution of the extract of cannabis leaves in acetone to a tube with a volume of 1.0 mL through a liquid-feeding pump at 90° C. at a flow rate of 0.033 mL/min.

FIG. 23 shows a UPLC chromatogram for analyzing cannabinoid ingredients in a processed product obtained by microwave-irradiation for 30 min while applying a 200 ppm solution of the extract of cannabis leaves in acetone to a tube with a volume of 1.0 mL through a liquid-feeding pump at 90° C. at a flow rate of 0.033 mL/min.

Figure 24:
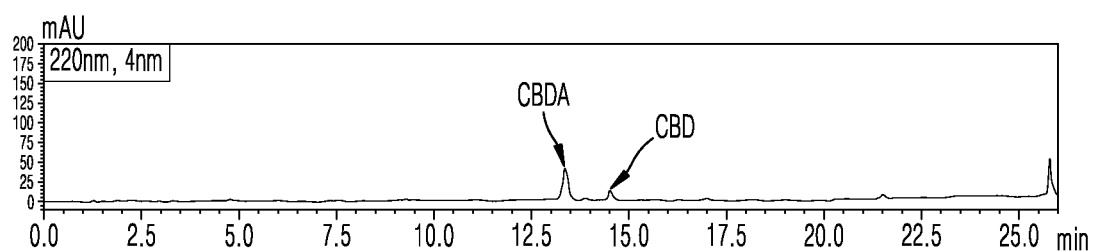
FIG. 24 shows a UPLC chromatogram for analyzing cannabinoid ingredients in a processed product obtained by microwave-irradiation for 30 minutes while applying a 200 ppm solution of the extract of cannabis leaves in hexane to a tube with a volume of 1.0 mL through a liquid-feeding pump at 90° C. at a flow rate of 0.033 mL/min.

FIG. 24 shows a UPLC chromatogram for analyzing cannabinoid ingredients in a processed product obtained by microwave-irradiation for 30 min while applying a 200 ppm solution of the extract of cannabis leaves in hexane to a tube with a volume of 1.0 mL through a liquid-feeding pump at 90° C. at a flow rate of 0.033 mL/min.

Figure 25:
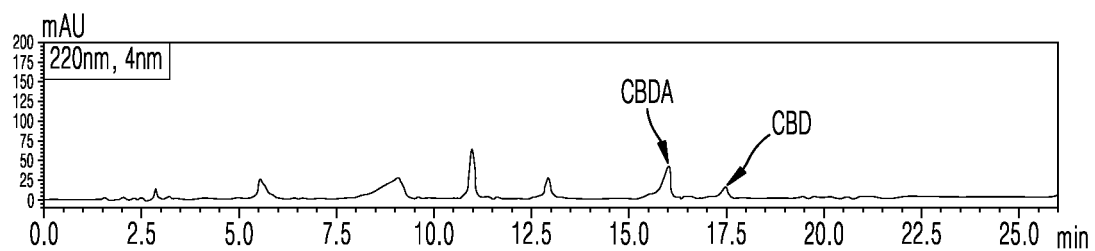
FIG. 25 shows a UPLC chromatogram for analyzing cannabinoid ingredients in a processed product obtained by microwave-irradiation for 30 minutes while applying a 200 ppm solution of the extract of cannabis leaves in 1,2-dichloroethane to a tube with a volume of 1.0 mL through a liquid-feeding pump at 90° C. at a flow rate of 0.033 mL/min.

FIG. 25 shows a UPLC chromatogram for analyzing cannabinoid ingredients in a processed product obtained by microwave-irradiation for 30 min while applying a 200 ppm solution of the extract of cannabis leaves in 1,2-dichloroethane to a tube with a volume of 1.0 mL through a liquid-feeding pump at 90° C. at a flow rate of 0.033 mL/min.

Figure 26:
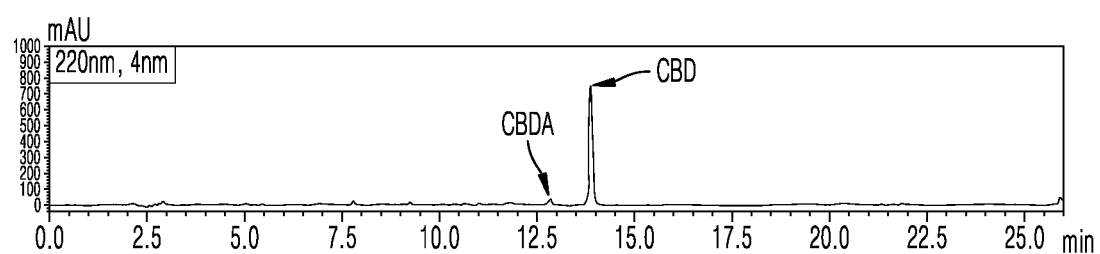
FIG. 26 shows a UPLC chromatogram for analyzing cannabinoid ingredients in a processed product obtained by microwave-irradiation for 30 minutes while applying a 10,000 ppm solution of the extract of cannabis leaves in ethanol to a tube with a volume of 1.0 mL through a liquid-feeding pump at 90° C. at a flow rate of 0.033 mL/min.

FIG. 26 shows a UPLC chromatogram for analyzing cannabinoid ingredients in a processed product obtained by microwave-irradiation for 30 min while applying a 10,000 ppm solution of the extract of cannabis leaves in ethanol to a tube with a volume of 1.0 mL through a liquid-feeding pump at 90° C. at a flow rate of 0.033 mL/min.

Figure 27:
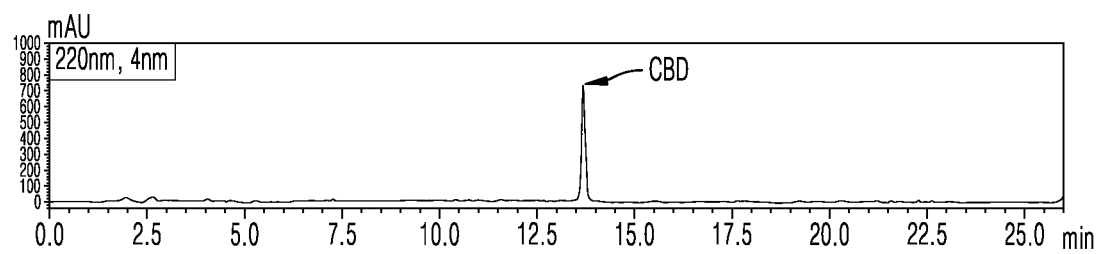
FIG. 27 shows a UPLC chromatogram for analyzing cannabinoid ingredients in a processed product obtained by microwave-irradiation for 30 minutes while applying a 10,000 ppm solution of the extract of cannabis leaves in ethanol to a tube with a volume of 1.0 mL through a liquid-feeding pump at 95° C. at a flow rate of 0.033 mL/min.

FIG. 27 shows a UPLC chromatogram for analyzing cannabinoid ingredients in a processed product obtained by microwave-irradiation for 30 min while applying a 10,000 ppm solution of the extract of cannabis leaves in ethanol to a tube with a volume of 1.0 mL through a liquid-feeding pump at 95° C. at a flow rate of 0.033 mL/min.

Further, the results of calculating the contents of CBDA and CBD in UPLC chromatograms obtained by continuous microwave processing of the cannabis extracts are summarized in Table 1.

TABLE 1

| Item | Temperature (° C.) – time (min) | CBDA | CBD | CBDA + CBD | CBD yield* | CBD content % = {CBD/(CBDA + CBD)} × 100 |
|---|---|---|---|---|---|---|
| Example 1 | — | 68.2 mg | 8.9 mg | 77.1 mg | 13.0% | 11.5% |
| Example 3 | 70-10 | 55.0 mg | 17.6 mg | 72.6 mg | 25.6% | 24.2% |
| Example 4 | 70-20 | 46.9 mg | 25.1 mg | 72.0 mg | 36.5% | 34.9% |
| Example 5 | 80-10 | 40.6 mg | 31.4 mg | 72.0 mg | 45.7% | 43.6% |
| Example 6 | 80-20 | 25.8 mg | 41.2 mg | 67.0 mg | 60.0% | 61.5% |
| Example 7 | 80-40 | 10.3 mg | 55.3 mg | 65.5 mg | 80.5% | 84.3% |
| Example 8 | 80-60 | 4.3 mg | 58.2 mg | 62.4 mg | 84.7% | 93.1% |
| Example 9 | 90-10 | 17.4 mg | 50.0 mg | 67.4 mg | 72.8% | 74.2% |
| Example 10 | 90-20 | 6.3 mg | 59.3 mg | 65.6 mg | 86.3% | 90.3% |
| Example 11 | 90-30 | n.d** | 63.7 mg | 63.7 mg | 92.8% | 100% |
| Example 12 | 90-40 | n.d** | 62.1 mg | 62.1 mg | 90.4% | 100% |
| Example 13 | 90-60 | n.d** | 58.9 mg | 58.9 mg | 85.7% | 100% |
| Example 14 | 100-5 | 25.4 mg | 36.9 mg | 62.3 mg | 53.7% | 59.2% |
| Example 15 | 100-10 | n.d** | 58.7 mg | 58.7 mg | 85.4% | 100% |

*CBD yield = (CBD mg / 68.7 mg (Theoretical CBD amount at 100% conversion) × 100
**n.d = not detected Table 1 shows CBDA and CBD contents expressed in mg per 1 g of the extract, after dissolving the cannabis leaf extract of Example 1 in ethanol at a concentration of 200 ppm and processing by continuous microwave irradiation. In the initial cannabis leaf extract (Example 1), cannabinoids were found to include 68.2 mg of CBDA and 8.9 mg of CBD, indicating that CBDA is 11.5%. According to the temperature and time of the continuous microwave irradiation, a decarboxylation reaction occurred to convert CBDA into CBD, and as a result, the content of CBD in the processed product was increased. The experiments were carried out at a microwave processing temperature from 70° C. to 100° C. with 5° C. to 10° C. intervals, and measurement was carried out from 5 min to 60 min to examine the effect of time on temperature. That is, as the processing temperature and time increased, the conversion to CBD tended to increase, and 100% of CBDA was completely converted to CBD at 90° C. after 30 min, and the CBD yield was 90.8%. Thereafter, the actual CBD yield tended to decrease. 100% of CBDA was also completely converted to CBD at 100° C. after 10 min, but the actual CBD yield was 85.4%.

Further, Table 2 summarizes the results of calculating the contents of CBDA and CBD in UPLC chromatograms obtained after continuous microwave processing of the cannabis extracts according to solvents.

TABLE 2

| Item | Solvent | CBDA | CBD | CBDA + CBD | CBD yield* | CBD content % = {CBD/(CBDA + CBD)} × 100 |
|---|---|---|---|---|---|---|
| Example 1 | — | 68.2 mg | 8.9 mg | 77.1 mg | 13.0% | 11.5% |
| Example 11 | EtOH | n.d** | 63.7 mg | 63.7 mg | 92.8% | 100% |
| Example 16 | BuOH | 28.2 mg | 36.3 mg | 64.5 mg | 52.8% | 56.3% |
| Example 17 | IPA | 40.4 mg | 27.4 mg | 67.9 mg | 39.9% | 40.4% |
| Example 18 | 80% EtOH | 2.2 mg | 28.0 mg | 30.2 mg | 40.8% | 92.7% |
| Example 19 | EtOAc | 68.1 mg | 8.4 mg | 76.5 mg | 12.2% | 11.0% |
| Example 20 | MeCN | 68.0 mg | 8.3 mg | 76.3 mg | 12.1% | 10.9% |
| Example 21 | acetone | 64.0 mg | 10.9 mg | 74.9 mg | 15.9% | 14.6% |
| Example 22 | hexane | 68.0 mg | 8.3 mg | 76.3 mg | 12.1% | 11.0% |
| Example 23 | DCE | 65.3 mg | 9.6 mg | 75.0 mg | 14.0% | 12.8% |

*CBD yield = (CBD mg / 68.7 mg (Theoretical CBD amount at 100% conversion) × 100
**n.d = not detected Table 2 shows CBDA and CBD contents expressed in mg per 1 g of the extract, after dissolving the cannabis leaf extract of Example 1 in each solvent at a concentration of 200 ppm and processing by continuous microwave irradiation under conditions of Example 11 (90° C., 30 min) in Table 1, where the highest CBD yield was observed. In Example 11, CBD yield was 92.8%. However, the low yields of 52.8%, 39.9% and 40.8% were observed in BuOH (butanol), IPA (isopropanol), and 80% EtOH aqueous solution, respectively, but the reaction was found to proceed.

However, it was found that the reaction hardly proceeded in ester-based solvents such as EtOAc (ethyl acetate), nitrile-based solvents such as MeCN (acetonitrile), ketone-based solvents such as acetone, hydrocarbon-based solvents such as hexane, and halogenated hydrocarbon-based solvents such as DCE(1,2-dichloroethane).

Further, Table 3 summarizes the results of calculating the contents of CBDA and CBD in UPLC chromatograms obtained after continuous microwave processing of high-concentration cannabis extracts.

TABLE 3

| Item | Temperature (° C.) – time (min) – concentration (ppm) | CBDA | CBD | CBDA + CBD | CBD yield* | CBD content % = {CBD/ (CBDA + CBD)} × 100 |
| --- | --- | --- | --- | --- | --- | --- |
| Example 1 | — | 68.2 mg | 8.9 mg | 77.1 mg | 13.0% | 11.5% |
| Example 11 | 90-30-200 | n.d** | 63.7 mg | 63.7 mg | 92.8% | 100% |
| Example 24 | 90-30-10,000 | 2.8 mg | 61.7 mg | 64.5 mg | 89.8% | 95.7% |
| Example 25 | 95-35-10,000 | n.d** | 62.9 mg | 62.9 mg | 91.5% | 100% |

CBD yield = (CBD mg / 68.7 mg (Theoretical CBD amount at 100% conversion) × 100
**n.d = not detected Table 3 shows CBDA and CBD contents expressed in mg per 1 g of the extract, after dissolving the cannabis leaf extract of Example 1 in ethanol at a concentration of 10,000 ppm and processing by continuous microwave irradiation under conditions of Example 11 (90° C., 30 min) in Table 1, where the highest CBD yield was observed. In Example 11, CBD yield was 92.8%. However, when the extract was reacted at a concentration of 10,000 ppm under the same conditions, CBD yield was 89.8%, and when the temperature was increased to 95° C., CBD was obtained with a high yield of 91.5%.

Consequently, according to the above method, the decarboxylation reaction proceeded with high yield within a short time at a low temperature of 100° C. or lower. In addition, a method of mass-producing a processed product having a high content of CBD was developed through the continuous microwave processing method.

As a result of the above experiments, when the cannabis extract was processed by the continuous microwave irradiation, CBDA which is a main cannabinoid component of the raw material cannabis may be more efficiently converted into CBD with excellent pharmaceutical efficacy, which has been proven in existing literatures, academic researches, patents, etc.

For example, it was possible to obtain a large amount of a microwave-irradiated processed product having a CBD content of 20% to 100%, based on the weight of the main cannabinoid components of cannabis leaves.

Experimental Example 2: CBD Production by Continuous Microwave Processing of Cannabis Extract (1) Experimental Method For an experiment to test 24-hour continuous reaction of the continuous reaction method, the ethyl acetate cannabis extract obtained in Example 1 was dried, and then dissolved at a concentration of 10,000 ppm in ethanol. By utilizing the conditions of Example 25 which are the optimum conditions for CBD production, the continuous reactor was set at a reaction temperature of 95° C., and microwave irradiation was carried out at a maximum microwave power of 45 W and a frequency of 2450 MHz for 30 min. Feeding was carried out for the total reaction time of 24 hr by setting the pump at a flow rate of 0.033 mL/min in the tube having an internal volume of 1.0 mL, and the power was 3 W to 45 W during microwave irradiation, and the content analysis was performed according to the analysis method of Experimental Example 1.

(2) Experimental Results

As a result of the experiment, ethanol was removed from 47.5 mL of the ethanol processed product treated for 24 hr using a vacuum evaporator, and the resulting concentrate was 475 mg, from which 32.5 mg of CBD was obtained by reverse-phase semi-preparative chromatography.

Consequently, continuous microwave processing was stably carried out under conditions of Example 25 for 24 hr, and 32.5 mg of CBD with purity of 99.2% was prepared through the decarboxylation reaction of CBDA.

Figure 28:
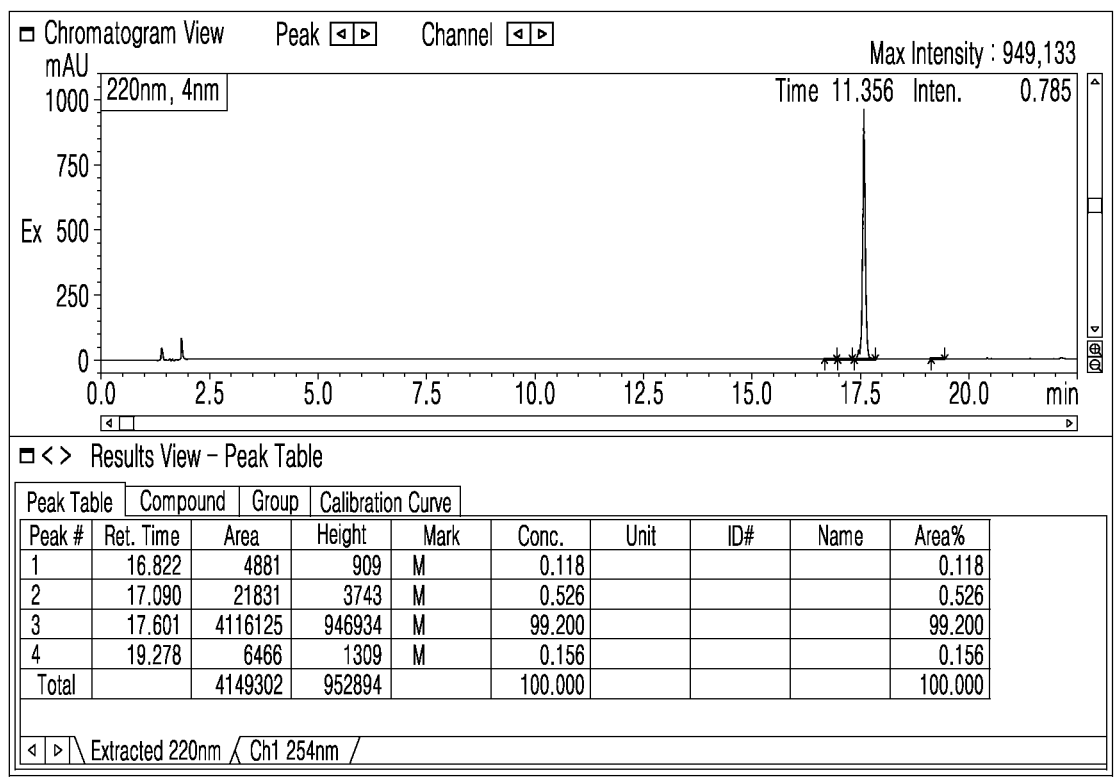
FIG. 28 shows a UPLC chromatogram for analyzing the purity of CBD isolated in Experimental Example 2.

FIG. 28 shows a UPLC chromatogram for analyzing the purity of CBD isolated from the processed product of Experimental Example 2.

According to the method of the present disclosure, CBDA included in the extract may be converted into CBD by continuous microwave irradiation. When the method is performed by microwave irradiation while applying the cannabinoid-including extract through a tubular container, the decarboxylation reaction of CBDA may be performed at high capacity per hour, and a product having a high CBD content of 20% to 100% may be efficiently produced.

A pharmaceutical composition including, as an active ingredient, cannabinoid isolated according to the method of the present disclosure may be used for anti-epilepsy, neuroprotection, vasorelaxation, anti-cancer, anti-inflammation, anti-diabetes, anti-bacteria, analgesia, anti-osteoporosis, immune enhancement, or antiemetic action.

A food composition including, as an active ingredient, cannabinoid isolated according to the method of the present disclosure may be used as a food, in particular, as a functional food.

A cosmetic composition including, as an active ingredient, cannabinoid isolated according to the method of the present disclosure may be used in a general cosmetics or functional cosmetics with antioxidant or anti-inflammatory functions.

It should be understood that embodiments described herein should be considered in a descriptive sense only and not for purposes of limitation. Descriptions of features or aspects within each embodiment should typically be considered as available for other similar features or aspects in other embodiments. While one or more embodiments have been described with reference to the figures, it will be understood by those of ordinary skill in the art that various changes in form and details may be made therein without departing from the spirit and scope of the disclosure as defined by the following claims.

What is claimed is:

1. A method of producing cannabinoids, the method comprising irradiating microwaves to a reaction mixture comprising an extract of *Cannabis* sp. in ethanol in a flow-through reaction vessel, wherein the microwave irradiation is carried out while passing the reaction mixture from an inlet of the reaction vessel to an outlet of the reaction vessel, wherein the reaction vessel is contained with a reaction chamber filled with a fluid to maintain a temperature of the reaction medium in a range from 80° C. to 100° C., wherein the extract includes cannabidiolic acid and the microwave irradiation is carried out for a time sufficient to convert the cannabidiolic acid to cannabidiol with a CBD yield of at least 84.7% and a CBD content % of at least 90.3%.

2. The method of claim 1, further comprising isolating cannabinoids from the microwave-irradiated reaction mixture.

3. The method of claim 1, wherein the extract is obtained by a method comprising contacting the *Cannabis* sp. plant with one or more of water, a protonic solvent, an aprotonic solvent, and a mixture thereof.

4. The method of claim 1, wherein the *Cannabis* sp. plant comprises leaves, flower buds, fruits, trichomes, flower bracts, stems, or any part comprising cannabinoids.

5. The method of claim 1, wherein the microwave irradiation is carried out for about 5 minutes to about 180 minutes.

6. The method of claim 1, wherein the microwave irradiation is carried out under pressure.

7. The method of claim 1, wherein the microwave irradiation is carried out at a frequency of 300 MHz to 300 GHz.

8. The method of claim 1, wherein the microwave irradiation is carried out at a power of 3 W to 6 kW.

9. The method of claim 1, wherein the reaction vessel is made of a microwave-transparent material.

10. The method of claim 1, wherein the reaction chamber comprises a microwave-transparent material.

11. The method of claim 1, wherein the microwave irradiation is carried out for a time sufficient to convert the cannabidiolic acid to cannabidiol with a CBD yield of at least 90.4% and a CBD content % of at least 93.1%.

* * * * *